United States Patent
Makovec et al.

[11] Patent Number: 5,976,576
[45] Date of Patent: Nov. 2, 1999

[54] PHARMACEUTICAL COMPOSITION FOR INHALATION CONTAINING CR 2039 (ANDOLAST)

[75] Inventors: Francesco Makovec; Paolo Senin; Lucio Claudio Rovati, all of Monza, Italy

[73] Assignee: Rotta Research Laboratories S.p.A., Monza, Italy

[21] Appl. No.: 09/129,794

[22] Filed: Aug. 6, 1998

[30] Foreign Application Priority Data

Aug. 8, 1997 [EP] European Pat. Off. ............. 97830417

[51] Int. Cl.⁶ ............................ A61K 9/14; A61K 31/41
[52] U.S. Cl. ........................................... 424/489; 514/381
[58] Field of Search .............................. 424/489; 514/381

[56] References Cited

U.S. PATENT DOCUMENTS

| | | | |
|---|---|---|---|
| 5,232,937 | 8/1993 | Makovec et al | 514/381 |
| 5,292,750 | 3/1994 | Yoshikuni et al. | 514/315 |
| 5,453,368 | 9/1995 | Tresco et al. | 435/182 |
| 5,648,096 | 7/1997 | Grander et al. | 424/489 |
| 5,741,168 | 4/1998 | Stroh et al. | 424/490 |
| 5,780,051 | 7/1998 | Eswara et al. | 424/449 |
| 5,855,913 | 1/1999 | Hanes et al. | 424/489 |

OTHER PUBLICATIONS

Revel et al, European Journal of Pharmacology, 229:45–53 (1992).

*Primary Examiner*—James H. Reamer
*Attorney, Agent, or Firm*—Sughrue, Mion, Zinn, Macpeak & Seas, PLLC

[57] ABSTRACT

A pharmaceutical composition comprising, as active ingredient, N-4-(1H-tetrazol-5-yl)phenyl-4-(1H-tetrazol-5-yl)benzamide disodium salt (CR 2039, Andolast) or another pharmaceutically-acceptable salt thereof and a flavoring, and optionally including a pharmaceutically-acceptable inert carrier and/or a pharmaceutically-acceptable sweetener, the composition being suitable for administration by oral inhalation.

31 Claims, No Drawings

PHARMACEUTICAL COMPOSITION FOR INHALATION CONTAINING CR 2039 (ANDOLAST)

The subject of the present invention is a novel pharmaceutical composition of the compound N-4-(1H-tetrazol-5-yl)phenyl-4-(1H-tetrazol-5-yl)benzamide disodium salt (CR 2039, Andolast) or of another pharmaceutically-acceptable salt thereof, the composition being suitable for administration by oral inhalation.

CR 2039 is a compound having potent anti-allergic and anti-asthmatic activity, the pharmacological activities of which have already been described, for example, in Revel L. et al. (1992), *Eur. J. Pharmacol.* 229, 45–53 and in U.S. document No. 5 232 937.

Many drugs used in the treatment of disorders of the respiratory tract are administered by oral inhalation. However, the dispensing of CR 2039 as a micronized powder for administration by this route has involved considerable problems which limit its use, in spite of its potent pharmacological activity.

One of these problems is that CR 2039 is extremely bitter. Another considerable problem is that CR 2039 disodium salt, like other salts thereof, is a hygroscopic substance of which the particles tend to form aggregates easily. In fact, small particles are quite unstable thermodynamically in view of the high ratio between their surface area and the space they occupy. When the product is used in the form of a micronized powder, the aggregation phenomena therefore make it difficult in use to maintain a particle diameter of the substance of less than 5 microns, beyond which limit it is difficult for a substance to penetrate the air passages deeply in order to be absorbed and thus perform its pharmacological activity. Administration by this route has therefore been somewhat unpleasant for patients who have not demonstrated the expected benefit from the treatment.

The object of the present invention is to provide, for the treatment of asthma and other pathological conditions of the respiratory tract, a novel pharmaceutical composition comprising, as active ingredient, CR 2039 disodium salt or another pharmaceutically-acceptable salt thereof for administration by oral inhalation. This novel pharmaceutical composition comprises, in addition to the active ingredient, a flavouring such as, for example, menthol or peppermint oil or mixtures thereof, and may also contain one or more pharmaceutically-acceptable inert carriers as well as one or more suitable sweeteners. The use of flavourings such as, for example, menthol or peppermint oil is important for various reasons. In the first place their use masks the unpleasant taste of CR 2039, increasing "compliance" in relation to this preparation. In the second place, their appropriate use succeeds, in particular, in increasing both the respirable fraction of the drug, that is, the so-called "fine-particle fraction" and the uniformity of the dose of the drug administered.

The sweeteners may be selected from carbohydrates such as, for example, sucrose, fructose, glucose, mannitol, etc., or aspartame, sodium cyclamate, saccharin, sodium saccharin, etc.

The novel pharmaceutical composition comprises, as active ingredient, CR 2039, preferably in the form of the disodium salt, as a fine micronized powder having a particle diameter preferably of between 0.1 and 10 microns and an average diameter preferably of between 1 and 3 microns, and a flavouring, preferably menthol, which is present in the composition in a ratio by weight (weight/weight) of between 0.5% and 10%, preferably 3%, with reference to the weight of the active ingredient.

The pharmaceutical composition may comprise sweeteners, preferably sodium saccharin, which may be present in the composition in a ratio by weight (weight/weight) of between 1% and 30%, preferably between 10% and 20%, with reference to the weight of active ingredient.

The composition may also comprise one or more inert, water-soluble carrier, preferably lactose or dextrose, in a ratio by weight (weight/weight) of between 0.5 and 5 times the weight of the active ingredient.

The pharmaceutical composition of the invention is preferably prepared by dissolving the flavouring, for example, the menthol or peppermint oil, in a volatile, non-aqueous solvent such as, for example, ethyl ether or, preferably, methylene chloride and mixing this solution with the active ingredient in the ratios indicated above. The advantage of this method is that, after evaporation of the solvent, a homogeneous, free flowing, non-sticky mixture is thus obtained, in contrast to what occurs if the components are simply mixed dry. Moreover, with this method the tendency of the particles of the active ingredient to form aggregates is greatly reduced.

As stated above, the composition may include an inert carrier such as, for example, lactose or dextrose, and a sweetener or, preferably, both. In this case, these components are mixed by conventional techniques with the active ingredient, flavoured as described above.

If inert carriers and sweeteners are used, these may also be mixed dry with the active ingredient beforehand, the resulting mixture then being treated with the organic solution containing the flavouring. Upon completion, the solvent is evaporated by conventional techniques.

The pharmaceutical composition according to the invention may be used as it is, by means of a conventional portable inhaler for dry powders. Alternatively, in order to increase the fluidity of the pharmaceutical composition within the reservoir of the inhaler device, the mixture can be transformed in pellets by tumbling it with conventional techniques and sieved through stainless steel sieves to provide pellets having a size between 100–1000 micrometers. Alternatively, hard gelatine capsules filled with the pharmaceutical composition of the invention may be used. The capsules are loaded into a conventional single- or multi-dose inhaler which, after the capsule has been suitably perforated, enables the contents of the capsule to be dispensed in a suitable manner for inhalation by the patient.

The invention is illustrated further by the following examples which should not, however, be considered in any way limiting of the invention.

1. Example of a Pharmaceutical Composition for Oral Inhalation Containing 8 mg of CR 2039 Disodium Salt Per Dose Administered

| Components | Quantity (mg) | % (weight/weight) |
|---|---|---|
| CR 2039 (micronized) | 8.0 | 50 |
| Menthol | 0.24 | 1.5 |
| Lactose | 7.26 | 45.375 |
| Sodium saccharin (micronized) | 0.50 | 3.125 |
| Total | 16.00 | 100 |

Preparation for 10000 Doses 2.4 g of menthol dissolved in 50 ml of methylene chloride were added to 80 g of CR 2039 disodium salt. After mixing, 72.6 g of lactose and 5 g of micronized sodium saccharine were added to the homogenous mass, again with stirring. The homogeneous mixture was dried under vacuum until the solvent had disappeared. The composition containing 50.0% of active ingredient could be used by filling hard gelatine capsules in quantities of 16.0 mg/capsule for dispensing by means of a suitable inhaler after perforation of the capsule, or could be used as it was, by filling a loader with a powder-holding chamber with the same quantity of mixture and dispensing it to the patient by inhalation by means of a suitable device for delivering powders.

2. Example of Pharmaceutical Composition for Oral Inhalation Containing 4 mg or CR 2039 Sodium Salt Per Dose Administered

| Components | Quantity (mg) | % (weight/weight) |
|---|---|---|
| CR 2039 (micronized) | 4.0 | 50 |
| Menthol | 0.12 | 1.5 |
| Dextrose | 3.88 | 48.5 |
| Total | 8.0 | 100 |

Preparation for 10000 Doses 38.8 g of dextrose were added to 40 g of micronized CR 2039 sodium salt. After mixing, 1.2 g of menthol dissolved in 25 ml of methylene chloride was added slowly to the homogeneous mass with stirring. The homogeneous mixture thus obtained was dried under vacuum until the solvent disappeared. The method described above in Example 1 was then followed in order to be able to dispense 8.0 mg of mixture containing 50% of active ingredient to the patient.

Naturally, the proportions of the components may be varied by an expert in accordance with the foregoing text.

What is claimed is:

1. A pharmaceutical composition comprising, as an active ingredient, N-4-(1H-tetrazol-5-yl)phenyl-4-(1H-tetrazol-5-yl)benzamide disodium salt (CR 2039, Andolast) or another pharmaceutically-acceptable salt thereof, and a flavouring, wherein said composition optionally also comprises a pharmaceutically-acceptable inert, water-soluble carrier, or a pharmaceutically-acceptable sweetener, or both a pharmaceutically-acceptable inert, water-soluble carrier and a pharmaceutically-acceptable sweetener, and wherein said composition is in a form suitable for administration by oral inhalation.

2. The pharmaceutical composition according to claim 1, wherein said active ingredient is CR 2039 disodium salt.

3. The pharmaceutical composition according to claim 1, wherein said flavouring is selected from the group consisting of menthol and peppermint oil, and said flavouring is present in a ratio by weight of between 0.5 and 10% based on the weight of the active ingredient.

4. The pharmaceutical composition according to claim 1, wherein said composition also comprises said sweetener, which is selected from the group consisting of sucrose, fructose, glucose, mannitol, aspartame, sodium cyclamate, acid saccharin, sodium saccharin and mixtures thereof.

5. The pharmaceutical composition according to claim 1, wherein said composition also comprises said inert, water-soluble carrier.

6. The pharmaceutical composition according to claim 1, wherein said composition comprises both a sweetener selected from the group consisting of sucrose, fructose, glucose, mannitol, aspartame, sodium cyclamate, acid saccharin, sodium saccharin and mixtures thereof, and an inert, water-soluble carrier selected from the group consisting of lactose and dextrose.

7. The pharmaceutical composition according to claim 4, wherein said sweetener is present in a ratio by weight of between 1% and 30% based on the weight of the active ingredient.

8. The pharmaceutical composition according to claim 5, wherein said inert, water-soluble carrier is present in a ratio by weight, of between 0.4 and 4 times the weight of the active ingredient.

9. A method of preparing a pharmaceutical composition comprising, as an active ingredient, N-4-(1H-tetrazol-5-yl)phenyl-4-(1H-tetrazol-5-yl)benzamide disodium salt (CR 2039, Andolast) or another pharmaceutically-acceptable salt thereof, and a flavouring, wherein said composition optionally also comprises a pharmaceutically-acceptable inert, water-soluble carrier, or a pharmaceutically-acceptable sweetener, or both a pharmaceutically-acceptable inert, water-soluble carrier and a pharmaceutically-acceptable sweetener, wherein said method comprises the steps of:

(A) admixing a flavouring solution with said active ingredient, wherein said flavouring solution comprises said flavouring dissolved in a volatile, non-aqueous solvent, and (B) evaporating any residual solvent.

10. The method according to claim 9, wherein prior to said admixing, said active ingredient is mixed with a sweetener selected from the group consisting of sacrose, fructose, glucose, mannitol, aspartame, sodium cyclamate, acid saccharin, sodium saccharin and mixtures thereof and with an inert, water-soluble carrier.

11. The method according to claim 9, wherein said active ingredient is CR 2039 disodium salt, said flavouring is methanol, said sweetener is sodium saccharin, and said inert, water-soluble carrier is lactose.

12. The pharmaceutical composition according to claim 7, wherein said sweetener is present in a ratio by weight of between 10% and 20% based on the weight of the active ingredient.

13. The pharmaceutical composition according to claim 7, wherein said sweetener is sodium saccharin.

14. The pharmaceutical composition according to claim 12, wherein said sweetener is sodium saccharin.

15. The pharmaceutical composition according to claim 8, wherein said inert, water-soluble carrier is lactose or dextrose.

16. An oral inhalation multidose, refillable device for delivering dry powders, wherein said device comprises a pharmaceutical composition according to claims 1, 2, 3, 4, 5, 6, 7, 8, 12, 13, 14, or 15.

17. An oral inhalation multidose, refillable device for delivering dry powders consisting of microfine pellets having a diameter of from about 100 to 1000 micrometers, wherein said device comprises a pharmaceutical composition according to claims 1, 2, 3, 4, 5, 6, 7, 8, 12, 13, 14, or 15 in the form of said pellets.

18. A hard gelatine capsule comprising a pharmaceutical composition according to claims 1, 2, 3, 4, 5, 6, 7, 8, 12, 13, 14 or 15 for use with a suitable device for delivering dry powders for oral inhalation.

19. A method for administering N-4-(1H-tetrazol-5-yl)phenyl-4-(1H-tetrazol-5-yl)benzamide disodium salt (CR 2039, Andolast) to a subject, comprising orally inhaling a composition comprising, as an active ingredient, CR 2039 (Andolast) or another pharmaceutically-acceptable salt thereof, and a flavouring, wherein said composition optionally also comprises a pharmaceutically-acceptable inert, water-soluble carrier, or a pharmaceutically-acceptable sweetener, or both a pharmaceutically-acceptable inert, water-soluble carrier and a pharmaceutically-acceptable sweetener.

20. The method according to claim 19, wherein said active ingredient is CR 2039 disodium salt.

21. The method according to claim 19, wherein said flavouring is selected from the group consisting of menthol and peppermint oil, and said flavouring is present in a ratio by weight of between 0.5 and 10% based on the weight of the active ingredient.

22. The method according to claim 19, wherein said composition also comprises said sweetener, which is selected from the group consisting of sucrose, fructose, glucose, mannitol, aspartame, sodium cyclamate, acid saccharin, sodium saccharin and mixtures thereof.

23. The method according to claim 19, wherein said composition also comprises said inert, water-soluble carrier.

24. The method according to claim 19, wherein said composition comprises both a sweetener selected from the group consisting of sucrose, fructose, glucose, mannitol, aspartame, sodium cyclamate, acid saccharin, sodium saccharin and mixtures thereof, and an inert, water-soluble carrier selected from the group consisting of lactose and dextrose.

25. The method according to claim 22, wherein said sweetener is present in a ratio by weight of between 1% and 30% based on the weight of the active ingredient.

26. The method according to claim 23, wherein said inert, water-soluble carrier is present in a ratio by weight of between 0.4 and 4 times the weight of the active ingredient.

27. The method according to claim 25, wherein said sweetener is present in a ratio by weight of between 10% and 20% based on the weight of the active ingredient.

28. The method according to claim 25, wherein said sweetener is sodium saccharin.

29. The method according to claim 27, wherein said sweetener is sodium saccharin.

30. The method according to claim 26, wherein said inert, water-soluble carrier is lactose or dextrose.

31. The method according to claim 13, wherein said sweetener is selected from the group consisting of sucrose, fructose, glucose, mannitol, aspartame, sodium cyclamate, acid saccharin, sodium saccharin and mixtures thereof, and said inert, water-soluble carrier is selected from the group consisting of lactose and dextrose.

* * * * *